United States Patent [19]

Ball

[11] Patent Number: 4,609,369

[45] Date of Patent: Sep. 2, 1986

[54] INTRAVENOUS SOLUTION ADMINISTRATION APPARATUS AND METHOD

[75] Inventor: Dean M. Ball, Gainesville, Ga.

[73] Assignees: John Fontana, Beaufort, S.C.; Don Fontana, Bethesda, Md.

[21] Appl. No.: 699,569

[22] Filed: Feb. 8, 1985

[51] Int. Cl.⁴ .................... A61M 31/00; A61M 37/00

[52] U.S. Cl. .................................... 604/56; 604/89; 604/410; 604/416; 206/219

[58] Field of Search ................ 604/82, 87, 89, 91-92, 604/262, 410, 416, 56; 206/219-221

[56] References Cited

U.S. PATENT DOCUMENTS

| | | | |
|---|---|---|---|
| 2,495,942 | 1/1950 | Nosik | 604/416 |
| 2,907,329 | 10/1959 | Cohen | 604/89 |
| 3,306,327 | 2/1967 | Ilg | 604/262 |
| 3,696,919 | 10/1972 | Miles | 604/416 |
| 3,726,276 | 4/1973 | Schumann et al. | 604/92 |
| 3,924,741 | 12/1975 | Kachur et al. | 604/92 |
| 4,061,144 | 12/1977 | Strickman et al. | 604/262 |
| 4,264,007 | 4/1981 | Hunt | 206/219 |
| 4,315,570 | 2/1982 | Silver et al. | 604/410 |
| 4,470,505 | 9/1984 | Korwin et al. | 206/219 |
| 4,483,439 | 11/1984 | Steigerwald et al. | 206/219 |
| 4,484,920 | 11/1984 | Kaufman et al. | 604/87 |

*Primary Examiner*—C. Fred Rosenbaum
*Assistant Examiner*—Michelle N. Lester
*Attorney, Agent, or Firm*—Thomas & Kennedy

[57] ABSTRACT

Intravenous solution administration apparatus comprises a container having flexible walls and a cup mounted to one of the flexible walls within the container with an open cup end located distal the one wall. A cap is mounted to another one of the flexible walls within the container for movement into and out of sealing engagement with the cup open end. The container also has a channel by which fluid may be drawn from the container.

9 Claims, 5 Drawing Figures

INTRAVENOUS SOLUTION ADMINISTRATION APPARATUS AND METHOD

TECHNICAL FIELD

This invention relates to methods and apparatuses for administering solutions intravenously.

BACKGROUND OF THE INVENTION

Today, intravenous or I.V. solution administration sets are widely employed in infusing solutions directly into the veins of clinical patients. Typically, an administration set includes a flexible bag which is suspended at a height above the patient and which contains the solution to be administered. To feed the solution from the bag into the patient by gravity, a cannula is inserted into a sealed guide tube that extends downwardly out of the bottom of the bag. A feed tube extends from the cannula through a metering device, such as an adjustable clamp, to a needle that is injected into the patient. The cannula usually has a hollow prong or spike formed with one or more orifices which penetrates into the interior of the bag. The lower end of the spike extends down into a drip chamber where the solution drip or flow rate may be visibly observed.

Some medications that are administered through the use of I.V. administration sets of the type just described cannot be premixed. Others have a very short shelf life and thus may not be prepared substantially in advance of the time in which they are to be administered. In these situations it has been necessary to maintain medication ingredients segregated in separate containers in advance of and often during their administration. In a hospital environment this can be highly inefficient as where nurses or other hospital personnel have to mix solutions together in proper proportions at the time that they set up an administration set and connect it with a patient.

As a result of the foregoing, administration sets have heretofore been devised that have two compartments or chambers in which solutions or particulated fluids may be maintained separately in advance of their being mixed together at the time of administration. One type of these sets, as disclosed in U.S. Pat. No. 4,325,368, is constructed so that segregated liquids may be fed independently at mutually different rates into a common feed line without having to be premixed. Some mixing may inherently occur with this type of set, but only to a limited degree. In another type of administration set, such as that disclosed in U.S. Pat. Nos. 4,392,850 and 4,392,851, an in-line mixing procedure is made possible by which a sterile, powdered material such as freeze dried antibiotic may be mixed with a solvent. This type of in-line apparatus, however, is relatively complicated to manufacture and therefore expensive. With its compartments being in-line, one above the other, it is difficult to effect thorough mixing. Thus, they have had to be manually pumped and inverted for effective mixing. Even then such mixing remains difficult due to the fact that fluid communication between compartments is established only through an elongated, relatively narrow and restricted channel. Since many hospital personnel also do not have good mechanical dexterity, consistency in such preparations is difficult to obtain and to be relied upon.

It thus is seen that a need exists for apparatuses and methods of administering medications that overcomes the just described limitations of the prior art. It is to the provision of such, therefore, that the present invention is directed.

SUMMARY OF THE INVENTION

In one form of the invention an intravenous solution administration apparatus comprises a container having flexible walls, a cup mounted to one of the flexible walls within the container with an open cup end located distal the one wall, and a cap mounted to another one of the flexible walls within the container for movement into and out of sealing engagement with the cup open end. Channel means are also included by which fluid may be drawn from the container.

In another form of the invention an intravenous solution administration apparatus comprises a container having a first, flexible plastic wall formed with a first opening and a second flexible plastic wall located opposite the first wall formed with a second opening located opposite the first opening. A relatively rigid cup is mounted to the first container wall sealing closed the first opening and which has an open cup end located within the container. A relatively rigid cup cap is mounted to the second wall sealing closed the second opening. So constructed, intravenous solution constituents may be stored in mutual isolation within the container with the cup open end closed by the cap and the two stored constituents later mixed together with the cap removed from the cup open end.

In yet another form of the invention a method of administering an intravenous solution comprises the steps of housing a first fluid within a cup mounted to open flexible wall of a container with an open end of the cup located within the container; releasibly sealing closed the cup open end with a cup cap mounted to another flexible wall of the container; housing a second fluid within the container about the sealed cup; pulling the cap off of the cup thereby establishing fluid communication between the cup interior and the container interior; mixing the first and second fluids; and withdrawing the mixed fluids from the container.

DETAILED DESCRIPTION

Figure 3:
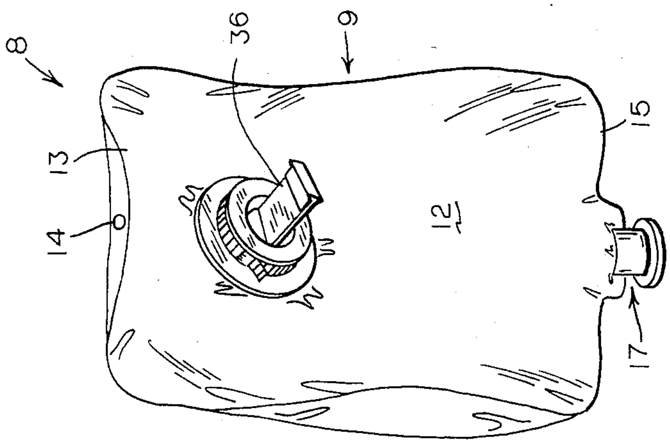
FIG. 3 is a side elevational view of the side of the administration set located opposite the side shown in FIG. 1.

With reference next to the drawing, an intravenous solution administration set 8 is shown that has a fluid tight, flexible container indicated generally at 9 formed with a flexible, plastic wall 11 sealed about its periphery to another flexible, plastic wall 12. The upper sealed edges 13 of the container are formed with a hole 14 by which the container may be suspended from an I.V. stand. The bottom edges 15 of the container are sealed to themselves. A conventional channel 17 is provided here that has a pierceable seal 18 through which a cannula may be inserted in fluid tight relation for drawing fluid out from the flexible container.

Figure 2:
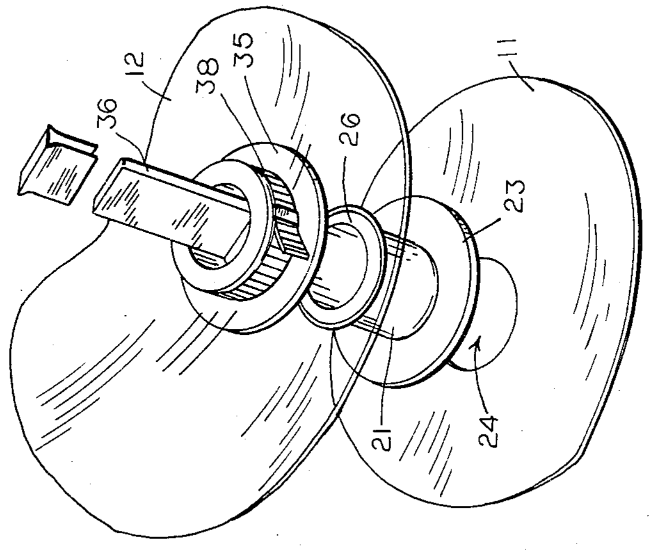
FIG. 2 is an exploded view, in perspective, of mating cup and cap components of the administration set illustrated in FIG. 1.
Figure 1:
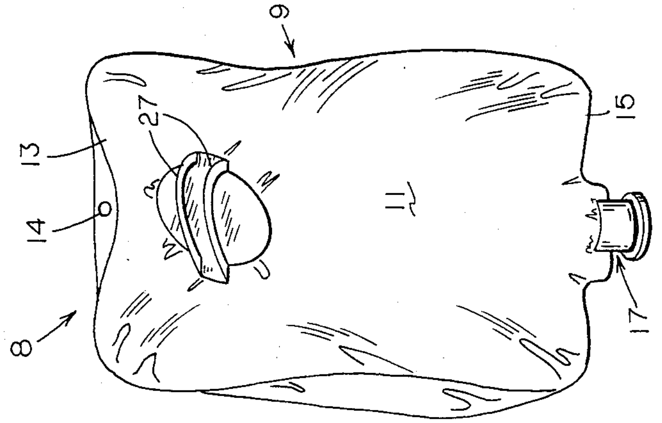
FIG. 1 is a side elevational view of an intravenous solution administration set or apparatus that embodys principles of the present invention.

With continued reference to the drawing the I.V. administration set is further seen to include a relatively rigid, plastic cup indicated generally at 20 that has an annular side wall 21 which extends into the interior of the container from an annular opening 24 formed in the container side wall 11. The cup has a disc-shaped bottom 22 formed with an annular flange 23 that overlays and is sealed to the periphery of wall 11 about the opening 24. Thus, in FIG. 2 the wall 11 is shown below the flange 23 solely for clarity of illustration. The cup has an open end, indicated generally at 25, where its side wall 21 is formed with an annular lip 26. A pair of pull tabs 27 extends outwardly from the cup bottom 22.

The administration set is further seen to include a relatively rigid, plastic cap, indicated generally at 30, that has a disc-shaped, central portion 31 of a size to be received within the interior of the cup wall 21. The cap also has an annular channel, indicated generally at 33, located about the central portion which is sized to receive the cup annular side wall 21 therewithin with the side wall lip 26 being in sealing engagement with the channel. The cap also has a peripheral flange 35 which underlays and is sealed to that portion of the flexible wall 12 which is located about the periphery of an annular hole therein which is in general alignment with the hole 24 formed in the other side wall 11. The cap further includes a pull tab 36 that projects outwardly from the central portion 31 exteriorly of the container.

Figure 4:
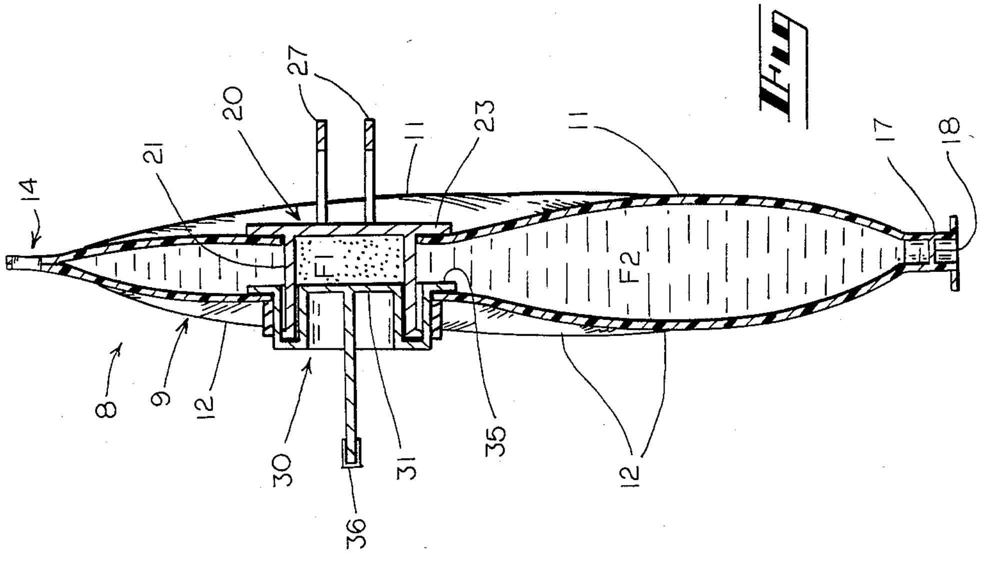
FIG. 4 is a cross-sectional view of the administration set shown in FIGS. 1–3 with the set cup sealed closed by the set cap.

In preparing the set for use the cup 20 is filled with a first fluid indicated at F1 in FIG. 4, with the upper edges of 13 of the container not yet sealed. This fluid may, for one example, be a freeze-dried antibiotic. The cap 30 is then pushed into sealing engagement with the cup thereby isolating the interior of the cup and the fluid F1 from the remainder of the interior of the container. This is easily done since the container walls are flexible and as yet not totally sealed. A safety strap 38 is then wrapped about and drawn down about the cap causing it to grip tightly the open cup end. A second fluid F2, such as a liquid solvent, is then poured into the open top of the container about the sealed cup. The top of the container is then sealed with the fluids F1 and F2 now isolated from each other. The I.V. solution administration set is now configured as shown in FIG. 4.

Figure 5:
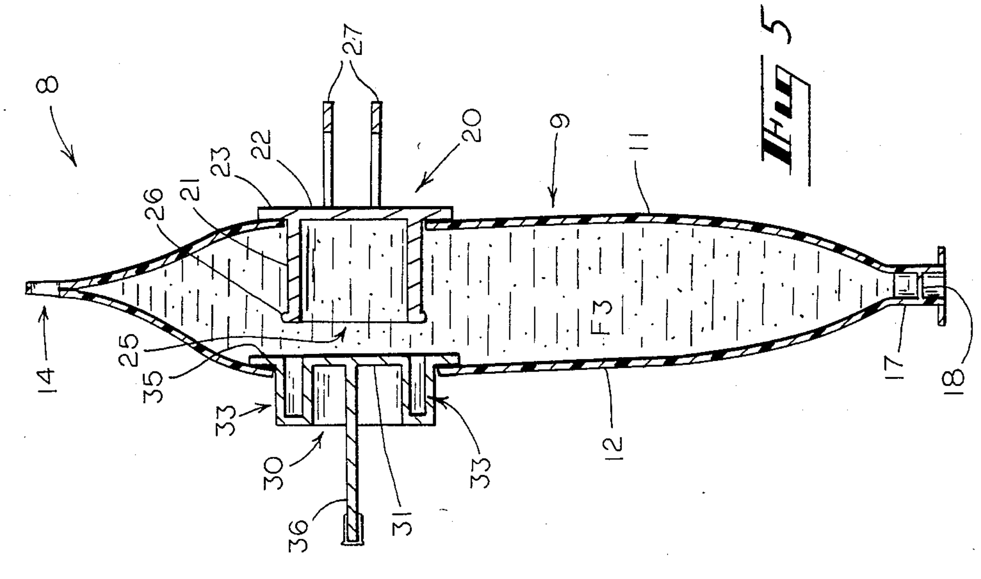
FIG. 5 is another cross-sectional view of the administration set illustrated in FIGS. 1–3 with the set cup unsealed by the set cap.

For use, the filled administration set 8 is suspended from an unshown I.V. stand. Just prior to infusion of medication the safety strap 38 is removed and the pull tabs 27 are gripped with one hand and the other pull tab 36 gripped with another hand and then manually pulled apart. As this is done the cap is pulled off of the open end of the cup 20 thereby establishing fluid communication between the interior of the cup and the remaining interior of the container. The set 8 is then shaken to cause the fluids F1 and F2 to be mixed and thereby form a resultant mixture F3. The set is now configured as shown in FIG. 5. An unshown cannula may then be inserted into the channel 17 at the bottom of the container so as to pierce the seal 18 and thereby establish means for draining the fluid F3 from the administration set and into a vein.

It thus is seen than an intravenous solution administration apparatus and method is provided which overcomes problems associated with those of prior art. It should, however, be understood that the just described embodiment merely illustrates principles of the invention in a preferred form. Many modifications, additions and deletions may, of course, be made thereto without departure from the spirit and scope of the invention as set forth in the following claims.

I claim:

1. Intravenous solution administration apparatus comprising a container having flexible walls; a cup mounted to one of said flexible walls within said container with an open cup end located distal said one wall; a cap mounted to another one of said flexible walls within said container for movement into and out of sealing engagement with said cup open end; channel means by which fluid may be drawn from said container; a first pull tab extending from said cup exteriorly said container, and a second pull tab extending from said cap exteriorly of said container.

2. The intravenous solution administration apparatus of claim 1 wherein said cup has a cylindrical wall and wherein said cap has a cylindrical channel in which at least a portion of said cup cylindrical wall may be releasibly seated.

3. The intravenous solution administration apparatus of claim 2 wherein said cup cylindrical wall is formed with a resilient annular lip at said open cup end of a size for sealing engagement within said cylindrical cap channel.

4. Intravenous solution administration apparatus comprising a container having a first flexible plastic wall formed with a first opening and a second flexible plastic wall located opposite said first wall formed with a second opening located opposite said first opening; a relatively rigid cup mounted to said first wall sealing closed said first opening and having an open cup end located within said container; a relatively rigid cup cap mounted to said second wall sealing closed said second opening; whereby two intravenous solution constituents may be stored in mutual isolation within said container with the cup open end closed by the cap and the two stored constituents later mixed together with the cap removed from the cup open end.

5. The intravenous solution administration apparatus of claim 3 wherein said cup has a flange that is sealed to said first sheet about the periphery of said first opening.

6. The intravenous solution administration apparatus of claim 4 wherein said cap has a flange that is sealed to said second sheet about the periphery of said second opening.

7. A method of administering an intravenous solution comprising the steps of:

(1) housing a first fluid within a cup mounted to one flexible wall of a container with an open end of the cup located within the container;

(2) releasibly sealing closed the cup open end with a cup cap mounted to another flexible wall of the container;

(3) housing a second fluid within the container about the sealed cup;

(4) pulling the cap off of the cup thereby establishing fluid communication between the cup interior and the container interior;

(5) mixing the first and second fluids; and (6) withdrawing the mixed fluids from the container.

8. The intravenous solution administration method of claim 7 wherein step (4) the cap is pulled off of the cup by manually gripping and pulling apart pull tabs that extend from the cup and cap exteriorly of the container.

9. The intravenous solution administration method of claim 7 wherein step (4) a portion of the other flexible wall located adjacent the cap is pulled away from the cup open end as the cap is pulled off the cup.

* * * * *